United States Patent [19]

Grabley et al.

[11] Patent Number: 4,778,629
[45] Date of Patent: Oct. 18, 1988

[54] PROCESS FOR THE PREPARATION OF ACYLOXYBENZENESULFONIC ACIDS AND SALTS THEREOF

[75] Inventors: Fritz-Feo Grabley, Königstein; Gerd Reinhardt, Kelkheim; Georg Bäder, Hofheim am Taunus; Walter Rupp, Königstein, all of Fed. Rep. of Germany

[73] Assignee: Hoechst Aktiengesellschaft, Frankfurt am Main, Fed. Rep. of Germany

[21] Appl. No.: 922,277

[22] Filed: Oct. 23, 1986

[30] Foreign Application Priority Data

Oct. 26, 1985 [DE] Fed. Rep. of Germany ....... 3538143

[51] Int. Cl.$^4$ .................. C11C 3/00; C07C 69/17
[52] U.S. Cl. .................. 260/402; 260/505 R; 560/142
[58] Field of Search .............. 260/400, 505 R, 402; 560/142

[56] References Cited

U.S. PATENT DOCUMENTS

| 4,038,328 | 7/1977 | Pelster | 260/505 R |
| 4,537,724 | 8/1985 | McKinnie et al. | 260/400 |
| 4,588,531 | 5/1986 | Balzer et al. | 560/142 |

FOREIGN PATENT DOCUMENTS

| 0098129 | 1/1984 | European Pat. Off. |  |
| 0098021 | 1/1984 | European Pat. Off. |  |
| 0105673 | 4/1984 | European Pat. Off. |  |
| 0125641 | 11/1984 | European Pat. Off. |  |
| 666626 | 9/1938 | Fed. Rep. of Germany |  |
| 2602510 | 8/1976 | Fed. Rep. of Germany | 560/142 |
| 1010058 | 4/1983 | U.S.S.R. | 560/142 |

OTHER PUBLICATIONS

Thomas, R. J., Ind. and Engin. Chem., 32, 408–410 (1940).
Luczyn, S., Chem. Abs., 91:107806 (1979).

*Primary Examiner*—J. E. Evans

[57] ABSTRACT

A process for the preparation of acyloxybenzenesulfonic acids and salts thereof, of the formula

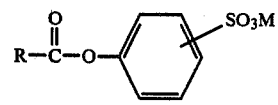

in which R is $C_1$–$C_{17}$-alkyl or $C_2$–$C_{17}$-alkenyl and M is an alkali or alkaline earth metal, ammonium or hydrogen, including the stages of (a) sulfonation of phenol, if appropriate (b) thermal treatment of the sulfonated phenol, (c) esterification of the sulfonated phenol and if appropriate (d) neutralization of the ester, wherein the sulfonation of the phenol is carried out with sulfuric acid or oleum and the water of reaction is removed during or after stage (b) by distillation and/or by reaction with a dehydrating agent.

14 Claims, No Drawings

PROCESS FOR THE PREPARATION OF ACYLOXYBENZENESULFONIC ACIDS AND SALTS THEREOF

The invention relates to the preparation of acyloxybenzenesulfonic acids and salts thereof in a multi-stage reaction sequence, starting from phenol and sulfuric acid or oleum.

Acyloxybenzenesulfonic acids and their salts are compounds which have been known for a long time and have surfactant properties and which, according to European patent No. 98,021, can also be used as perborate activators. A number of processes for their preparation have already been disclosed.

They can be obtained, for example, by reacting Na phenolsulfonate with acid chlorides (European patent No. 98,129), with anhydrides (European patent No. 105,673) or esters (European patent No. 125,641). The reactions proceed very slowly and must normally be carried out at a high temperature. In addition, the preparation of anhydrous Na phenolsulfonate is very cost-intensive. According to German patent No. 666,626, acyloxybenzenesulfonic acids are obtained by sulfonation of phenol esters.

The process described in DE-A No. 3,524,052 must, however, be regarded as the most economical process. This process takes place in four stages, namely (a) sulfonation of phenol with chlorosulfonic acid or SO$_3$,
(b) heat treatment of the phenolsulfonic acid in order to increase the proportion of the 4-isomer,
(c) esterification of the phenolsulfonic acid with a derivative of an organic acid (acid chloride or anhydride) or an organic acid in the presence of dehydrating agents (for example SOCL$_2$), and
(d) pH-controlled neutralization of the ester and, if appropriate, isolation of the salt, for example by spray-drying.

In this process, as distinct from the process according to the invention described below, the sulfonation is carried out with chlorosulfonic acid or SO$_3$, in order to obtain anhydrous phenolsulfonic acid.

The use of anhydrous phenolsulfonic acid is particularly important for the multi-stage reacion sequence described above for the preparation of acyloxybenzenesulfonic acids, since the acyloxybenzenesulfonic acid formed in stage (c) is readily hydrolyzed in the presence of water, which leads to a drastic reduction in yield.

Polish patent No. 99,682 (CA 91, 107,806) has disclosed that anhydrous phenolsulfonic acid can be obtained from phenol and sulfuric acid if the water of reaction, formed during the reaction, is removed from the reaction medium. This is effected by sulfonating phenol with H$_2$SO$_4$ and dripping the sulfonation mixture through a column with a heating jacket, in which a counter-current gas stream of an inert organic solvent, for example C$_7$H$_{16}$, azeotropically removes the water of reaction. The disadvantages of this process are the expense for equipment and the expensive separation of the organic solvent from the reaction product. According to Ind. eng. Chem. 32, 408 (1940), the water of reaction can also be removed by addition of BF$_3$ to the reaction mixture, by distillation in the form of BF$_3$. 2 H$_2$O, but the BF$_3$ must then be recovered via Ca(BF$_4$)$_2$ in a downstream stage.

It is the object of the present invention to develop a process, which is easy to implement even on a large industrial scale, for the preparation of acyloxybenzenesulfonic acids or salts thereof, phenolsulfonic acid being obtained in stage (a) from phenol and sulfuric acid or oleum and being dehydrated in a later stage.

The invention relates to a process for the preparation of acyloxybenzenesulfonic acids and salts thereof, of the formula

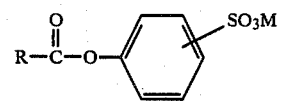

in which R is C$_1$–C$_{17}$-alkyl or C$_2$–C$_{17}$-alkenyl and M is an alkali or alkaline earth metal, ammonium ion or hydrogen, including the stages of (a) sulfonation of phenol, if appropriate (b) thermal treatment of the sulfonated phenol, (c) esterification of the sulfonated phenol and, if appropriate (d) neutralization of the ester, the sulfonation of the phenol being carried out with sulfuric acid or oleum and the water of reaction being removed during or after the heat treatment by distillation and/or by reaction with a dehydrating agent.

The sulfonation of the phenol is carried out with 50 to 100% sulfuric acid, preferably 96 to 98% sulfuric acid, or with oleum having an SO$_3$ content of 20% or 65%. If sulfuric acid is used, the reaction temperature is between 30° and 150° C., preferably between 50° and 110° C. If oleum is used the reaction temperature is between 30° and 110° C., preferably between 30° and 60° C. The quantity of sulfuric acid or oleum for the sulfonation is chosen such that there are 0.8 to 1.2 mol, preferably 0.95 to 1.1 mol, of sulfonating agent per 1 mol of phenol. The sulfonation reaction can be carried out in the absence of a solvent or in the presence of 5 to 120 mol % (relative to phenol) of a C$_2$–C$_{18}$-alkanoic acid, for example 3,5,5-trimethylhexanoic acid. The subsequent removal of the water by distillation is considerably accelerated by the presence of this acid.

The further reaction of the phenolsulfonic acid thus obtained to give the acyloxybenzenesulfonic acid is as described in DE-A No. 3,524,052. Depending on the composition of the phenolsulfonic acid mixture, a heat treatment of the phenolsulfonic acid may take place. In this heat treatment, the phenolsulfonic acid is treated thermally in such a way that the proportion of 4-phenolsulfonic acid relative to the proportion of 2-phenolsulfonic acid and hence also in absolute terms increases. For this purpose the phenolsulfonic acid formed is heated to a temperature of, in particular, 50° to 110° C. During this heat treatment, the proportion of the 4-isomer rises (relative to the quantitative proportion of the 2-isomer) from about 2–3 to 1 without a heat treatment stage to preferably about 8–20 to 1 (depending on the heat treatment conditions).

The heat treatment time is in general 0.5 to 10 hours. This heat treatment can, however, also be omitted, in particular if the phenolsulfonic acid mixture already has the desired ratio of the 2- and 4-isomers from the start.

Subsequently thereto or during the heat treatment stage, the water of reaction formed is removed either by distillation or by addition of a dehydrating agent However, both methods can also be applied together, in which case the water of reaction is first largely removed by distillation and an after-treatment of the reaction mixture with a dehydrating agent is then carried out. The distillation takes place under normal pressure or under reduced pressure and can, like the sulfonation be carried out continuously or discontinuously. The desired residual water content is here at most 5% by weight.

If the sulfonation is carried out with 65 percent oleum, a further reduction of the water content is achieved by the addition of 0.3 to 0.5 mol of a dehydrating agent such as, for example, $SOCL_2$ or with 0.1 to 0.25 mol of $POCl_3$, $PCl_3$, $P_4O_{10}$ or similar compounds. When sulfuric acid is used, the quantity of the dehydrating agent depends on the residual water content in the phenolsulfonic acid. In order to ensure sufficient reaction of these dehydrating agents with the residual water, this step is carried out at temperatures of 30° to 120° C. and a reaction time of 15 minutes to 6 hours, preferably 30 minutes to 2 hours. If thionyl chloride is used, the temperature is preferably 30° to 60° C. and for $P_4O_{10}$ it is 60° to 90° C. If the hydrolysis products formed at this temperature are gaseous, they can be removed from the sulfonation mixture by means of an inert gas or by reduced pressure. If these are solid or liquid by-products, they can remain in the sulfonation mixture so that, for example when dehydrating phosphorus compounds are used, the end product then contains $NaH_2PO_4$ or $Na_2H_2P_2O_7$ after stage (d).

The combination of both process steps, i.e. initially distilling off the major part of the water of reaction and then binding the residual water by addition of a dehydrating agent, is particularly advantageous in the case that the sulfonation is carried out with sulfuric acid. In the event of sulfonation with oleum, it is in most cases sufficient to remove the water of reaction by adding a dehydrating agent.

In the subsequent acylation stage (c), the anhydrous phenolsulfonic acid is esterified, the phenolsulfonic acids of stages (a) or (b) being reacted with ($C_2$-$C_{18}$-alkanoic acid halides (in particularchlorides) or anhydrides without additives, or with the free acids or their anhydrides in the presence of dehydrating agents such as $SOCl_2$ or $POCl_3$. This stage can be carried out in the pesence of aprotic organic solvents, but in particular a solvent-free variant is also successful. The reaction temperature is in general 0° to 110° C., preferably 20° to 80° C., and the reaction time is 0.5 to 8 hours. The quantity of acylating agent used is preferably 0.8 to 1.2, in particular 0.9 to 1.1 mol, per mol of sulfonic acid; if anhydrides are used, this quantity is reduced to 0.4 to 0.6 mol. The dehydrating agent used is as a rule added in a slight excess. Since the occurrence of foam must occasionally be expected in the esterification, it is advisable in these cases to add an antifoam based, for example, on a silicone. The esterification stage can be followed by an after-treatment with $SOCl_2$ or $POCl_3$. The preferred suitable acylating agents are compounds derived from a $C_6$-$C_{18}$-alkanoic acid, for example from isononanoic acid (3,5,5-trimethylhexanoic acid), nonanoic acid, 2-ethylhexanoic acid, dodecanoic acid, hexadecanoic acid and octadecanoic acid. The hydrocarbon radicals of these compounds can be saturated or unsaturated and straight-chain or branched; the carboxyl group or a functional group derived from the former can also be a substituent within the hydrocarbonyl radical, but preferably it is terminal. In practice the alkanoic acids are frequently mixtures of compounds of different chain lengths or they contain greater or lesser amounts of unsaturated compounds, but they should on average be within the above range.

If appropriate—provided that preparation of the salts is intended—the acylation stage (c) is then followed by a neutralization stage (d) in which the sulfonic acid group is converted into the salt form. The neutralization—preferably in an aqueous medium—is carried out at controlled pH values, in order to prevent as far as possible any hydrolysis of the acyloxybenzenesulfonic acids formed in stage (c); it can be run in the range from pH 2 to 7.5, but a range from 3 to 6 is preferred. In this stage, the temperature is advantageously 0° to 50° C., and the bases used are, for example, alkali metal, alkaline earth metal or ammonium hydroxides, carbonates or bicarbonates.

The product obtained after the end of stage (d) is then dried, for example by spray-drying. The process according to the invention can be carried out discontinuously, and also continuously in equipment customary in this field.

Compared with the state of the art, the process according to the invention has in particular the following advantages:

Due to the use of $H_2SO_4$ or oleum, the sulfonation can be carried out in less complicated equipment, even on a large industrial scale, than in the case of using $CLSO_3H$ or $SO_3$.

The formation of by-products (for example sulfones or sulfonic acid esters) is markedly suppressed by the water formed in the reaction mixture during the sulfonation, so that an acyloxybenzenesulfonic acid of higher quality is obtained.

In the examples which follow, parts by weight have the same relation to parts by volume as kg to $dm^3$ and, unless otherwise stated, % data are always by weight. The term AS content in the examples which follow is to be understood as the proportion of active substance in the product, which is determined by 2-phase titration according to EPTON.

COMPARATIVE EXAMPLE V 1

The example describes the preparation and conversion of phenolsulfonic acid from phenol and oleum, without removal of the water of reaction.

94 parts by weight of phenol are melted at a temperature of 40° to 45° C. 89.7 parts by weight of 65% oleum are then added dropwise with cooling in such a way that the reaction temperature does not exceed 50° C., and the mixture is then stirred for 2 hours at 80° C.

At a temperature of 45° to 50° C., 182 parts by weight of isononanoic acid chloride are then added dropwise to the sulfonation mixture within 1 hour, and the reaction mixture is stirred for one further hour; during and after the end of this stage (c), care is taken to ensure that the HCl gas forming is discharged. The reaction product, obtained in virtually quantitative yield, has an AS content of 68%; after standing for 6 hours at 25° C., the reaction product then has a content of only 52%.

EXAMPLE 1

The procedure followed is as indicated in comparison example V 1, but 40 parts by weight of thionyl chloride are added before the esterification and the mixture is stirred for one further hour at 80° C. The isononanoyloxybenzenesulfonic acid has an AS content of 81.9%, which is stable for several days. The Na salt as the end product has an AS content of 83%.

EXAMPLE 2

The procedure followed is as indicated in comparison example V 1, but 15.8 parts by weight of $P_2O_5$ are added before the esterification and the mixture is stirred for one further hour at 80° C. The isononanoyloxybenzenesulfonic acid has a stable AS content of 79.2%, and the Na salt as the end product has an AS content of 80%.

EXAMPLE 3

94 parts by weight of phenol are dissolved in 163 parts by weight of isononanoic acid. 89.7 parts by weight of 65% oleum are added dropwise with cooling in such a way that the reaction temperature does not exceed 50° C., and the mixture is then stirred for 2 hours at 80° C. At 45° to 50° C., 166 parts by weight of thionyl chloride are then added dropwise within 1 hour, and the mixture is stirred for 1 further hour. The isononanoyloxybenzenesulfonic acid has a stable AS content of 81%, and the Na salt obtained as the end product in virtually quantitative yield has an AS content of 84%.

COMPARATIVE EXAMPLE V 2

The example describes the preparation and conversion of phenolsulfonic acid which is obtained from phenol and sulfuric acid without removal of the water of reaction.

107 parts by weight of 96% sulfuric acid are added dropwise within 30 minutes to 94 parts by weight of phenol at a temperature between 40° and 50° C. The mixture is then stirred for a further 2 hours at 80° C. and 182 parts by weight of isononanoic acid chloride are then added dropwise at 40° to 45° C. within 1 hour and the mixture is stirred for 1 further hour. This gives an isononanoyloxybenzenesulfonic acid having an AS content of 40% which further drops on standing at 25° C.

EXAMPLE 4

94 parts by weight of phenol are dissolved in 166 parts by weight of isononanoic acid. 107 parts by weight of 96% sulfuric acid are then added to this solution and the mixture is heated for 30 minutes to 100° to 110° C. The water of reaction is then largely distilled off under reduced pressure (20 mm) within 30 minutes. After cooling, 134 parts by weight of thionylchloride are added dropwise at 45° to 50° C., with addition of an antifoam. The mixture is stirred for one further hour. This gives a stable isononanoyloxybenzenesulfonic acid havingan AS content of 81%, and the Na salt as the end product, which is obtained in virtually quantitative yield (relatative to phenol), has an AS content of 85%.

EXAMPLE 5

94 parts by weight of molten phenol are introduced and, at a temperature of up to 80° C., sulfonated with 103 parts by weight of 96% sulfuric acid within 30 minutes. The water of reaction is then largely distilled off under reduced pressure (20 mm) within 3 hours at 105° C. At 80° C., 16.7 parts by weight of $P_2O_5$ are then introduced, and the mixture is stirred for a further 30 minutes at 85° C. After cooling to 45° to 50° C., 188 parts by weight of isononanoic acid chloride are added dropwise within 30 minutes, and the mixture is stirred for a further 30 minutes. This gives an isononanoyloxybenzenesulfonic acid having an AS content of 79% and, after neutralization, an N salt having an AS content of 83% is isolated from this acid.

EXAMPLE 6

Initially, the procedure of example 5 is followed. After water has been distilled off under reduced pressure, 54.6 parts by weight of thionylchloride are added, and the mixture is stirred for a further 30 minutes at 80° C. Subsequently, the procedure of example 5 is again followed. This gives an isononanoyloxybenzenesulfonic acid having an AS content of 80% and an Na salt having an AS content of 83%.

We claim:

1. A process for the preparation of an acyloxybenzenesulfonic acid and salts thereof, of the formula

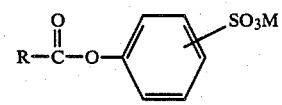

in which R is $C_1$-$C_{17}$-alkyl or $C_2$-$C_{17}$-alkenyl and M is an alkali metal, one equivalent of an alkaline earth metal, ammonium or hydrogen, including the stages of (1) sulfonation of phenol and (2) esterification of the sulfonated phenol, which comprises carrying out the sulfonation of the phenol with sulfuric acid or oleum and, subsequent to the completion of sulfonation step (1), but prior to esterification step (2), removing the water of reaction from the reaction mixture.

2. The process as claimed in claim 1, wherein the sulfonation reaction is carried out in the presence of 5 to 120 mol % of a $C_2$-$C_{18}$-alkanoic acid.

3. The process as claimed in claim 1, wherein a dehydrating agent is used which is thionyl chloride, phosphorus oxychloride, phosphorus trichloride or phosphorus pentoxide.

4. A process for the preparation of an acyloxybenzenesulfonic acid or salt thereof, of the formula

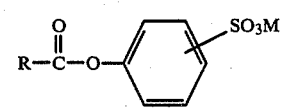

in which R is $C_1$-$C_{17}$-alkyl or $C_2$-$C_{17}$-alkenyl and M is an alkali metal, one equivalent of an alkaline earth metal, ammonium or hydrogen, comprising the steps of:
(1) sulfonation of phenol with sulfuric acid or oleum to obtain sulfonated phenol,
(2) subsequent to the completion of the sulfonation, removing the water of reaction, resulting from said step (1), to substantially dehydrate the sulfonated phenol, and
(3) esterifying the resulting dehydrated sulfonated phenol.

5. The process as claimed in claim 4, wherein the esterified product of said step (3) is neutralized to form a said salt, wherein M of said formula is an alkali metal, one equivalent of an alkaline earth metal or ammonium.

6. The process as claimed in claim 4, wherein the product of said step (1) is heat treated to increase the proportion of 4-phenolsulfonic acid relative to the proportion of 2-phenolsulfonic acid, and the said step (2) is carried out during or after this heat treatment.

7. The process as claimed in claim 4, wherein said step (2) comprises a distillation step.

8. The process as claimed in claim 7, wherein said step (1) is carried out in the presence of 5 to 120 mol-% of a $C_2$-$C_{18}$-alkanoic acid to accelerate the removal of water during said distillation step.

9. The process as claimed in claim 4, wherein said step (2) comprises the step of adding a dehydrating agent to the sulfonated phenol obtained in said step (1).

10. The process as claimed in claim 9, wherein the dehydrating agent is thionyl chloride, phosphorus oxychloride, phosphorus trichloride or phosphorus pentoxide.

11. The process as claimed in claim 9, wherein the water of reaction is reacted with a dehydrating agent which forms gaseous hydrolysis products at 30° to 120° C. and the gaseous hydrolysis products are removed from the acyloxybenzene sulfonic acid or salt end product.

12. The process as claimed in claim 9, wherein the water of reaction is reacted with a hydrating agent which forms liquid or solid hydrolysis products, and the hydrolysis products are permitted to remain in the acyloxybenzene sulfonic acid or salt end product.

13. The process as claimed in claim 4, wherein said step (2) is carried out by means of a combination of a distillation step and the addition of a dehydrating agent.

14. The process as claimed in claim 4, comprising the steps of:
 (1) sulfonation of phenol with sulfuric acid or oleum to obtain sulfonated phenol containing water of reaction;
 (2) subsequent to said sulfonation, removing at least a portion of the water of reaction resulting from said step (1) by adding to the reaction medium a dehydrating agent selected from the group consisting of thionyl chloride, phosphorus oxychloride, phosphorus trichloride or phosphorus pentoxide, thereby forming gaseous or liquid hydrolysis products; and
 (3) esterifying the resulting dehydrated sulfonated phenol with a carboxylic acid chloride or anhydride.

* * * * *